(12) United States Patent
Jordan et al.

(10) Patent No.: US 11,826,584 B2
(45) Date of Patent: Nov. 28, 2023

(54) SYSTEMS AND METHODS FOR USING LOW INTENSITY ULTRASONIC TRANSDUCER ON THE BRAIN

(71) Applicant: Synaptec Network, Inc, Santa Monica, CA (US)

(72) Inventors: Sheldon Jordan, Pacific Palisades, CA (US); Sergio Becerra, Cambridge, MA (US)

(73) Assignee: Synaptec Network, Inc., Santa Monica, CA (US)

( * ) Notice: Subject to any disclaimer, the term of this patent is extended or adjusted under 35 U.S.C. 154(b) by 0 days.

(21) Appl. No.: 16/840,638

(22) Filed: Apr. 6, 2020

(65) Prior Publication Data

US 2020/0315579 A1 Oct. 8, 2020

Related U.S. Application Data

(60) Provisional application No. 62/829,301, filed on Apr. 4, 2019.

(51) Int. Cl.
*A61B 8/00* (2006.01)
*A61N 7/00* (2006.01)

(52) U.S. Cl.
CPC ........ *A61N 7/00* (2013.01); *A61N 2007/0021* (2013.01); *A61N 2007/0091* (2013.01)

(58) Field of Classification Search
CPC ............ A61B 8/4227; A61B 2576/026; A61B 8/0808; A61B 8/4209; A61B 8/4477;
(Continued)

(56) References Cited

U.S. PATENT DOCUMENTS 5,409,005 A * 4/1995 Bissonnette ......... A61B 8/0808
600/437
5,515,728 A 5/1996 Casarcia
(Continued)

FOREIGN PATENT DOCUMENTS

CN 1212896 4/1999

OTHER PUBLICATIONS

Bowary et al., "Noninvasive Focused Ultrasound for Neuromodulation: A Review," Psychiatric Clinics of North America, vol. 41, Issue 3, Sep. 2018, pp. 505-514.
(Continued)

*Primary Examiner* — Christopher Koharski
*Assistant Examiner* — Taylor Deutsch
(74) *Attorney, Agent, or Firm* — Fish IP Law, LLP

(57) ABSTRACT

Methods, devices, and systems are disclosed for affixing and orienting an ultrasound transducer to a patient. A mount has a base, with a top surface, a bottom surface, an outer surface, and a plurality of internal surfaces. Some of the internal surfaces define a number of through holes that pass through the top surface and the bottom surface at the periphery or outer edge of the base. A number of supports are also arranged on the outer surface of the housing to affix the mount to the patient, to affix the transducer to the mount, or both. At least one of the plurality of internal surfaces defines a channel between the top and bottom surfaces proximal to a center of the mount, which receives a transducer and directs the transducer head toward the patient.

19 Claims, 7 Drawing Sheets

(58) Field of Classification Search
CPC ............ A61B 8/42–4236; A61B 90/50; A61N 2007/0021; A61N 7/00; A61N 2007/0026; A61N 2007/003; A61N 2007/0091
See application file for complete search history.

(56) References Cited

U.S. PATENT DOCUMENTS

| | | | |
|---|---|---|---|
| 8,603,014 B2 | 12/2013 | Alleman | |
| 2011/0251489 A1 | 10/2011 | Zhang | |
| 2012/0109019 A1* | 5/2012 | Schneider | ............... A61N 7/00 601/2 |
| 2013/0090688 A1* | 4/2013 | Montello | ........... A61B 17/7049 606/246 |
| 2013/0236961 A1 | 9/2013 | Amit et al. | |
| 2014/0188011 A1 | 7/2014 | Wurster et al. | |
| 2016/0367217 A1* | 12/2016 | Flores, II | ............. A61B 8/4227 |
| 2018/0169443 A1 | 6/2018 | Wurster | |

OTHER PUBLICATIONS

International Search Report dated Jul. 27, 2020, for related PCT Application No. PCT/US2020/026818, 4 pages.

Chetty, S. et al., "A simple tool to improve pluripotent stem cell differentiation", Nature Methods, Jun. 2013, vol. 10, No. 6, pp. 553-556 (internal pp. 1-14).

Sulistio, Y. A. et al., "Interleukin-6-Mediated Induced Pluripotent Stem Cell (iPSC)-Derived Neural Differentiation", Molecular Neurobiology, 2018, vol. 55, pp. 3513-3522.

Qiu, Z. et al., "Marmoset induced pluripotent stem cells: Robust neural differentiation following pretreatment with dimethyl sulfoxide", Stem Cell Research, 2015, vol. 15, pp. 141-150 A the whole document.

Ackermann, "A 3D iPSC-differentiation model identifies interleukin-3 as a regulator of early human hematopoietic specification" Haematologica. May 1, 2021; 106(5): 1354-1367. Published online Apr. 23, 2020. doi: 10.3324/haematol.2019.228064.

Bastidas, 2016, Cytokines TNF -?, IL-6, IL-17F, and IL-4 Differentially Affect Osteogenic Differentiation of Human Adipose Stem Cells, Hindawi Publishing Corporation, Stem Cells International, vol. 2016, Article ID 1318256, 9 pages.

Hwang, 2014, WNT3A promotes myogenesis of human embryonic stem cells and enhances in vivo engraftment, Sci Rep. Aug. 1, 2014;4:5916. doi: 10.1038/srep05916. PMID: 25084050; Pmcid: PMC5379990.

Khajeniazi*,, 2016, Synergistic induction of cardiomyocytedifferentiation from human bone marrow mesenchymal stem cells by interleukin 1β and 5-azacytidine, Biol Chem . Dec. 1, 2016;397(12):1355-1364. doi: 10.1515/hsz-2016-0151.

Lam, 2010, Activation of Interleukin-6-Induced Glycoprotein 130/ Signal Transducer and Activator of Transcription 3 Pathway in Mesenchymal Stem Cells Enhances Hepatic Differentiation, Proliferation, and Liver Regeneration, Liver Transplantation 16:1195-1206, 2010.

Tie, 2019, Interleukin-6 signaling regulates hematopoietic stem cell emergence. Exp Mol Med 51, 1-12 (2019). https://doi.org/10.1038/s12276-019-0320-5.

Xie, 2018, Interleukin-6/interleukin-6 receptor complex promotes osteogenic differentiation of bone marrow-derived mesenchymal stem cells, Stem Cell Res Ther. Jan. 22, 2018;9(1):13. doi: 10.1186/s13287-017-0766-0.

Kondo, 214, Histone Deacetylase Inhibitor Valproic Acid Promotes the Dilerentiation of Human Induced Pluripotent Stem Cells into Hepatocyte-Like Cells, Plos ONE 9(8): e104010. hhttps://doi.org/10.1371/journal.pone.0104010.

Noronha, 2109, Priming approaches to improve the efficacy of mesenchymal stromal cell-based therapies, Noronha et al. Stem Cell Research & Therapy (2019) 10:131 https://doi.org/10.1186/s13287-019-1224-y.

* cited by examiner

SYSTEMS AND METHODS FOR USING LOW INTENSITY ULTRASONIC TRANSDUCER ON THE BRAIN

This application claims priority to U.S. provisional application No. 62/829,301, filed Apr. 4, 2019, the disclosure of which is incorporated herein by reference.

FIELD OF THE INVENTION

The field of the invention is methods, systems, kits, and devices related to applying ultrasonic waves to the brain.

BACKGROUND

The background description includes information that may be useful in understanding the present invention. It is not an admission that any of the information provided herein is prior art or relevant to the presently claimed invention, or that any publication specifically or implicitly referenced is prior art.

Treatment of delicate, fragile, or complex regions of a patient's body typically requires great precision and accuracy. Such is the case with treatments of a patient's brain, where even slight deviation from a target in the brain can have negative impacts on the patient. Further, indirect treatment of sensitive brain matter is preferred where possible, as direct treatment is quite invasive and entails great risk. For example, "Noninvasive Focused Ultrasound for Neuromodulation: A Review" by Paul Bowary provides an overview of indirect treatment of specific regions of the brain by low intensity focused ultrasound. However, given the indirect treatment of such methods, it is very difficult to first target, with great precision, accuracy, and repeatability, specific regions of the brain with ultrasound, and to then adjust or refine the orientation of ultrasonic transducers to improve the targeting in a repeatable manner.

All publications identified herein are incorporated by reference to the same extent as if each individual publication or patent application were specifically and individually indicated to be incorporated by reference. Where a definition or use of a term in an incorporated reference is inconsistent or contrary to the definition of that term provided herein, the definition of that term provided herein applies and the definition of that term in the reference does not apply.

Attempts have been made to improve the targeting of indirect therapies on patients. For example, U.S. Patent Publication No. 2018/0169443 to Wurster attempts to improve precision and reproducibility of targeted ultrasonic therapy on a patient. However, Wurster '443 requires a patient be secured in place to a larger assembly while therapy is administered, and the extent to which the transducer can be oriented is limited. Similarly, US Patent Publication No. 2014/0188011 to Wurster, et al teaches freeing the patient from a large static assembly, and instead coupling a more mobile assembly to the patient's head. However, the degrees of adjustment and orientation of the ultrasonic transducer of Wurster '011 are still limited and appear to lack the level of precision, accuracy, and reproducibility that may be required for such therapies to pass regulatory approval.

Thus, there remains a need for systems and methods and devices to improve the accuracy, precision, and reproducibility of applying ultrasound therapies to targeted regions of the brain, as well as to correct or refine such targeting.

SUMMARY OF THE INVENTION

The inventive subject matter provides apparatus, systems, and methods for affixing a device to a patient. A mount has a base, with a top surface, a bottom surface (preferably substantially parallel to the top surface), an outer surface, and a plurality of internal surfaces. At least some of the internal surfaces define or makeup a number of through holes that pass through the top surface and the bottom surface of the periphery or outer edge of the base. A number of supports are also arranged on the outer surface of the housing, for example toward the upper surface of the base, to affix the mount to the patient. At least one of the plurality of internal surfaces defines a channel between the top and bottom surfaces proximal to a midpoint or center of the top surface. In some embodiments, the channel further has a collar that extends from the perimeter of the channel normal to the bottom surface of the base. The channel serves to receive the device, preferably directing an operable portion of the device (e.g., sonic transducer) normal to the bottom surface of the base or toward the patient (e.g., patient's head).

Methods of orienting a device affixed to a patient are also contemplated. The device is coupled (e.g, removably, replaceably, etc.) to a central channel of a mount (e.g., through hole, passes through two opposite surfaces of the mount, etc). The mount further has a first elevator, a second elevator, and a third elevator. The first elevator is used to adjust an elevation of the device with respect to the patient at a first point, the second elevator is used to adjust an elevation of the device with respect to the patient at a second point, and the third elevator is used to adjust an elevation of the device with respect to the patient at a third point. The first, second, and third elevators are each parallel or substantially coplanar to each other and the central channel, or both. The central channel directs an operable portion of the device toward the patient (e.g., normal to a bottom surface of the mount).

Systems for directing a device toward a target in a patient are also contemplated. A mount is affixed to the patient by a support and releasably coupled to the device via a central channel through the mount. A plurality of elevators are arranged along the mount (e.g., along a periphery or outer edge of the mount), such that the elevators and the central channel are parallel and substantially coplanar with each other. At least one of elevators is manipulated to direct the device (e.g., a ray normal to a surface of the device, acoustic waves from the device, etc) toward the target in the patient. The device is typically an ultrasonic transducer, and the central channel typically directs an operable portion of the device toward the patient. The mount is typically shaped like a partially eclipsed disk.

Multiple mounts of the inventive subject matter can be used to position and orient multiple devices, or a single mount can be used to orient more than one transducer, with respect to a patient.

Various objects, features, aspects, and advantages of the inventive subject matter will become more apparent from the following detailed description of preferred embodiments, along with the accompanying drawing figures in which like numerals represent like components.

DETAILED DESCRIPTION

Figure 1:
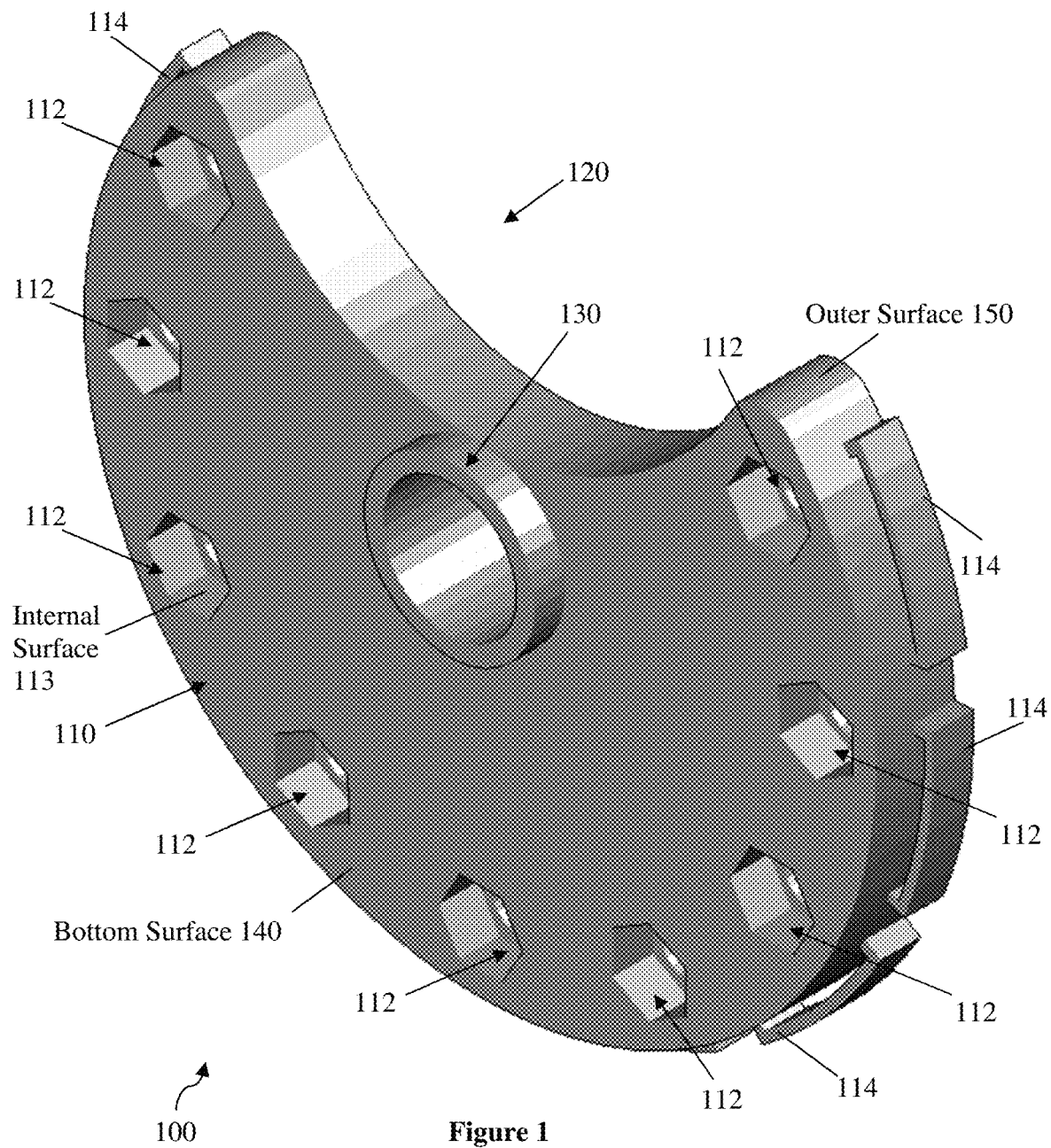
FIG. 1 depicts a mount of the inventive subject matter.

The inventive subject matter provides apparatus, systems, and methods for affixing a device to a patient. A mount has a base, with a top surface, a bottom surface (preferably substantially parallel to the top surface), an outer surface, and a plurality of internal surfaces. At least some of the internal surfaces define or makeup a number of through holes that pass through the top surface and the bottom surface at the periphery or outer edge of the base. A number of supports are also arranged on the outer surface of the housing, for example toward the upper surface of the base, to affix the mount to the patient. At least one of the plurality of internal surfaces defines a channel between the top and bottom surfaces proximal to a midpoint or center of the top surface. In some embodiments, the channel further has a collar that extends from the perimeter of the channel normal to the bottom surface of the base. The channel serves to receive the device, preferably directing an operable portion of the device (e.g., sonic transducer) normal to the bottom surface of the base or toward the patient (e.g., patient's head).

Preferably, the housing is substantially shaped as a disk or a partial disk. An elevator (e.g., bolt and nut, threaded screw, jack, riser, ratchet, detent, etc) is positioned in each (or most, or at least some) of the through holes to raise or lower a portion of the mount (e.g., proximal to the elevator) with respect to the patient. For example, an elevator in a through hole at a three o'clock position on the mount acts to raise and lower the mount at the three o'clock position. Likewise, an elevator in a through hole at a nine o'clock position on the mount acts to raise and lower the mount at the nine o'clock position. Raising and lowering elevators at the nine and three o'clock positions in conjunction can act to tilt a ray normal to the mount toward the nine o'clock position or toward the three o'clock position, or remain substantially normal as the mount is raised from or lowered to a surface of the patient's skull. Viewed from another perspective, a first elevator raises or lowers a first portion of the mount proximal to the first through hole, a second elevator raises or lowers a second portion of the mount proximal to the second through hole, and a third elevator raises or lowers a third portion of the mount proximal to the third through hole. Manipulation (raising or lowering) of the first, second, and third elevators affects, and at least partially controls, an orientation of the mount in three dimensions.

The through holes (e.g., axis of the through holes) are parallel and at least partially coplanar with each other. Preferably, three (or more) through holes are not points in the same straight line. In embodiments with more than three through holes, it is contemplated that some, half, most, or all of the through holes (e.g., axis of the through hole) are parallel and at least partially coplanar with each other, provided that a minimum of three through holes satisfy that condition. It is generally preferred that no more than two through holes as described exist in the same straight line.

The supports are used to attach and hold the mount on the patient. At least one support is a strap (e.g., elastic) coupled to a buckle, a button, a hook, a slot, a magnet, an adhesive, or a hook and loop coupling. In preferred embodiments, the supports affix the mount, and thereby the device in the mount, to the patient's head. The device is typically an acoustic transducer, more preferably an ultrasonic transducer (e.g., high frequency, low frequency, multi-frequency, etc). A first support at least partially affixes the mount to the patient, while a second support at least partially affixes the device to the mount. In some embodiments, the first support and the second support are the same.

Methods of orienting a device affixed to a patient are also contemplated. The device is coupled (e.g, removably, replaceably, etc.) to a central channel of a mount (e.g., through hole, passes through two opposite surfaces of the mount, etc). The mount further has a first elevator, a second elevator, and a third elevator. The first elevator is used to adjust an elevation of the device with respect to the patient at a first point, the second elevator is used to adjust an elevation of the device with respect to the patient at a second point, and the third elevator is used to adjust an elevation of the device with respect to the patient at a third point. The first, second, and third elevators are each parallel (or substantially parallel, or at least not perpendicular) or substantially coplanar to each other and the central channel, or both. The central channel directs an operable portion of the device toward the patient (e.g., normal to a bottom surface of the mount).

It is preferred that the three elevators are not in the same straight line, such that raising and lowering of the three elevators with respect to the patient acts to direct a ray normal to a surface of the device in three dimensions. A fourth elevator can be further used to adjust an elevation of the device with respect to the patient at a fourth point. It is contemplated that, where orientation of a ray normal to surface of the device must be highly precise, highly accurate, or highly repeatable, more than three (e.g., more than four, five, six, seven, eight, nine, ten, etc) through holes and associated elevators about the periphery of the device are used to achieve the requisite precision, accuracy, or repeatability, including delicate, slight, or minute adjustments as required. It should be appreciated that the inventive subject matter allows operators to achieve unprecedented precision, accuracy, and repeatability in directing devices toward targets in a patient, for example a target in the patient's brain.

In some embodiments, elevators used with the mount are configured to provide macro adjustments, micro adjustments, or both. Macro adjustments typically permit adjustments in the order of millimeters (e.g., 10 mm, 5 mm, 1 mm, 0.1 mm, etc) or centimeters (e.g., 10 cm 5 cm, 1 cm, 0.1 cm, etc.), while micro adjustments permit adjustments in the order of micrometers (e.g., 1 µm, 10 µm, 20 µm, 30 µm, 40 µm, 50 µm, 100 µm, etc) or millimeters (e.g., 0.1 mm, 0.2 mm, 0.3 mm, 0.4 mm, 0.5 mm, 0.6 mm, 0.7 mm, 0.8 mm, 0.9 mm, 1 mm, etc.). For example, a mount may include at least one macro adjustment elevator and at least one micro adjustment elevator. In some embodiments, elevators are arranged in pairs of macro and micro adjusters (e.g., nested/telescoping elevators), such that a pair of elevators adjust the mount in one direction in both macro and micro scales. Elevators are preferably arranged about the mount to enable micro and macro adjustments of the mount (e.g., ray normal to the central channel of the mount) in three dimensions.

The device used with or oriented by the mount is typically an ultrasound transducer, though other acoustic transducers or wave emitters can be used. Likewise, while the acoustic wave emitted by the transducer can be a continuous wave or a confluence of a plurality of waves, in preferred embodiments the acoustic wave is made up of a series of ultrasound pulses, for example pulses from more than one transducer. The elevators on the mount are used to orient the operable portion of the device to transmit the acoustic (e.g., ultrasonic) wave toward a target in the patient, for example a specific portion of an organ or a tissue of the patient (e.g., parts of the brain, etc.).

Systems for directing a device toward a target in a patient are also contemplated. A mount is affixed to the patient by a support and releasably coupled to the device via a central channel through the mount. A plurality of elevators are arranged along the mount (e.g., along a periphery or outer edge of the mount), such that the elevators and the central channel are parallel and substantially coplanar with each other. At least one of the elevators is manipulated to direct the device (e.g., a ray normal to a surface of the device, acoustic waves from the device, etc) toward the target in the patient. The device is typically an ultrasonic transducer, and the central channel typically directs an operable portion of the device toward the patient. The mount is typically shaped like a partially eclipsed disk.

Multiple mounts of the inventive subject matter can be used to position and orient multiple devices, or a single mount can be used to orient more than one transducer, with respect to a patient.

FIG. 1 depicts mount 100 of the inventive subject matter for use with one or more transducers. Mount 100 has a generally disc shaped body 110 with curved region 120. Viewed from another perspective, the mount is a partial disc with the appearance of the Sun during partial eclipse by the Moon. Body 110 of the mount has a top surface 160, a bottom surface 140 opposite the top, interior surfaces 113, and an exterior or outer surface 150. An interior surface towards the center of mount 100 defines a cross-sectionally circular and generally cylindrical channel 130 through the mount to receive or couple to an ultrasonic transducer. Channel 130 includes a raised rim or collar on the bottom surface of mount 100 that extends away from the bottom surface 140 (see FIGS. 1, 2, and 3), and a flush rim on the top surface 160 of mount 100 that is generally flush and coextensive with the top surface 160 (see FIGS. 4, 5, 6). A transducer used with mount 100 is typically oriented in the channel such that the transducer and resultant ultrasonic waves are directed toward the bottom surface, preferably in a direction substantially normal to the bottom surface. In some embodiments, the transducer is nested in curved region 120, with a portion of the transducer coupling with channel 130 to aid in orienting the transducer.

Eight supports 114 are positioned along the exterior surface toward the top surface of mount. Supports 114 are used to fix the mount to a patient (e.g., the head or skull of a patient), and can also be used to at least partially couple a transducer (e.g., ultrasound) to mount 100. For example, an ultrasound transducer is coupled to mount 100 in channel 130 (e.g., stem or base of transducer extends though channel with head of transducer positioned in the channel and flush with the raised rim or collar, or the transducer head having a diameter larger than the channel and resting on top of the raised rim or collar), and mount 100 itself is fixed to the patient's head using straps coupled to supports 114, with the straps further holding the ultrasonic transducer in place. In preferred embodiments, the straps are elastic or otherwise tensive, such that they press mount 100 towards the patient's head, in turn pressing channel 130 and the ultrasound transducer against the patient's head (e.g., raised rim or collar pressing transducer head against patient). It should be appreciated that maintaining contact of the ultrasound transducer with the flesh of the patient (e.g., head) is critical to effectively administer ultrasonic therapy to the patient.

Nine through holes 112 are arranged around the periphery (e.g., towards exterior surface) of mount 100. Here, through holes 112 are evenly spaced, substantially (if not completely) parallel (e.g., axis of through hole), and co-planar, and arranged such that a straight line cannot pass through the center of more than two through holes. Each through hole 112 (or most, or some, or at least three) receives an elevator (not depicted), preferably a bolt passing through the through hole and engaged with a nut nested in the hex portion of the through hole. Each elevator is used to adjust the distance of that respective part of mount 100 from the patient (e.g., patient's head), which in turn adjusts the orientation of the ultrasound device coupled to mount 100, which in turn steers or directs ultrasonic waves emitted by the ultrasound device. Thus, it should be appreciated that adjusting some, more preferably most, still more preferably all, of the elevators allows for a user to make very precise, very accurate, and very repeatable adjustments and refinements to the orientation and effective target of ultrasonic waves emitted by the transducer coupled to the mount.

Figure 2:
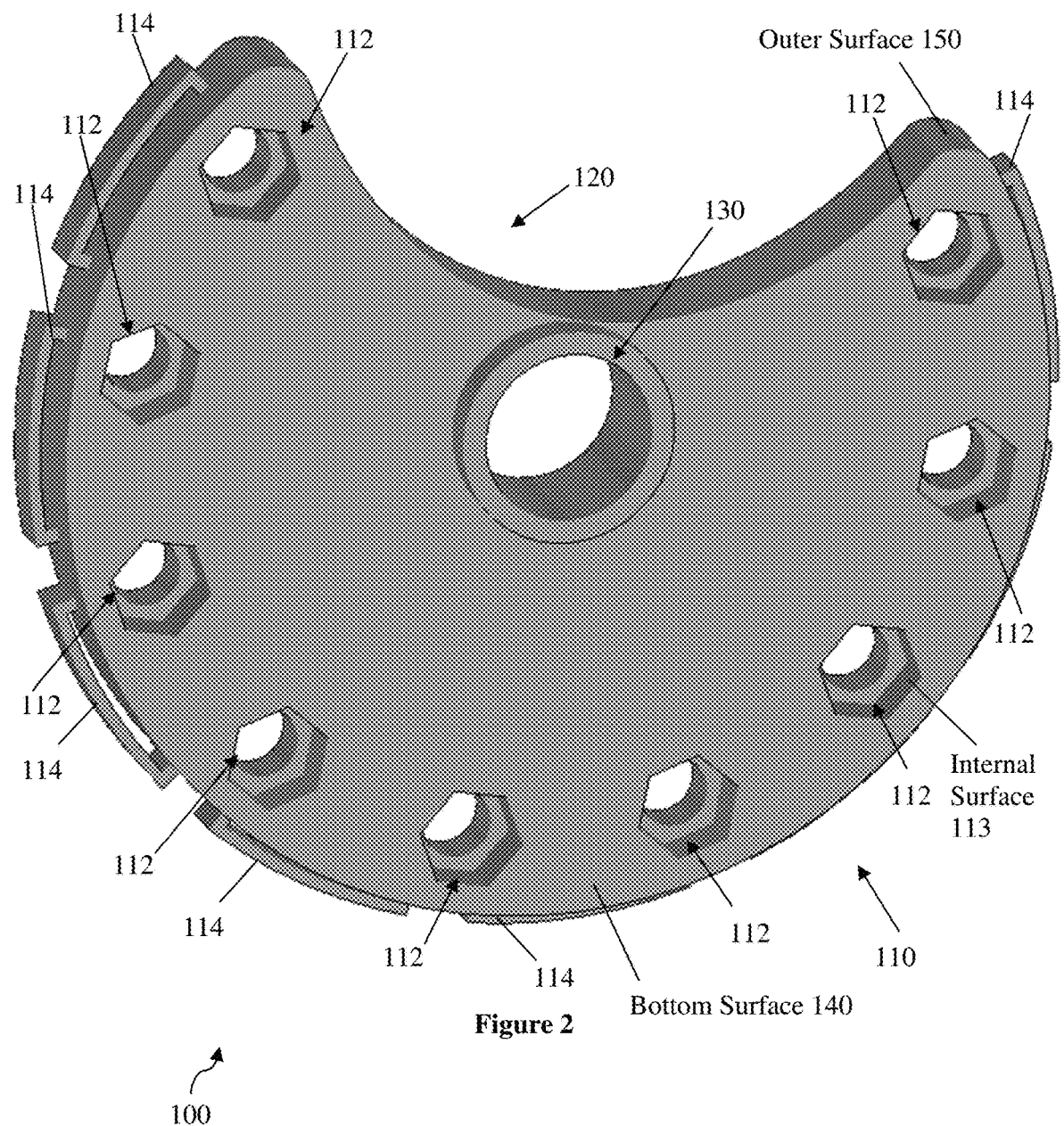
FIG. 2 depicts a different view of the mount of FIG. 1.
Figure 3:
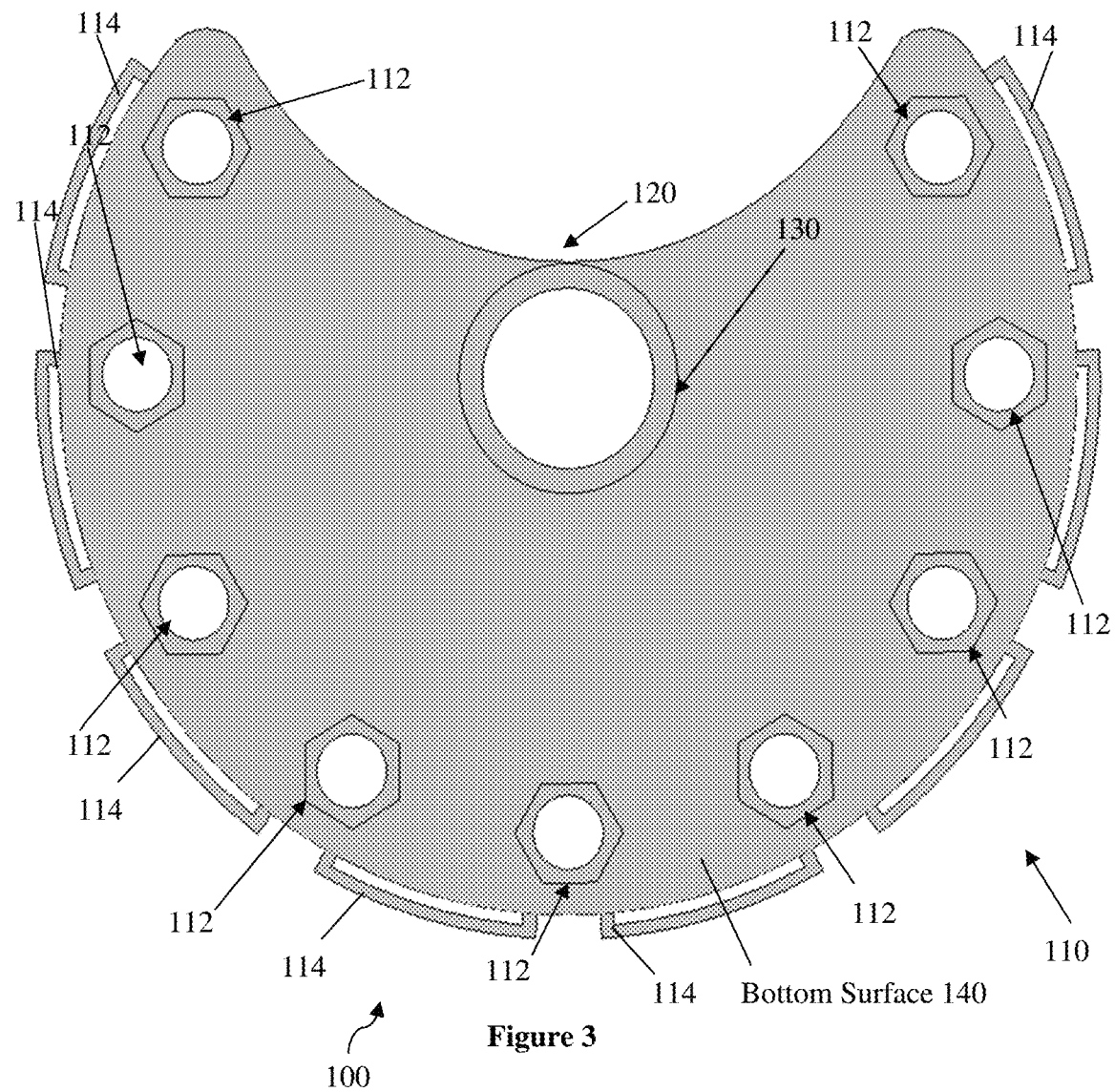
FIG. 3 depicts another view of the mount of FIG. 1.

As seen in FIGS. 1-3, each through hole 112 includes two tiers. The first tier of each through hole 112 is located toward and adjacent to the bottom surface of the mount, while the second tier is located toward and adjacent to the top surface. The first tier of each through hole 112 has a hexagonal or hexagonal prism shape, while the second tier has a substantially circular or cylindrical shape. The first tier diameter is also larger than the second tier diameter. When a bolt and nut (e.g., hexagonal nut conforming to shape of first tier of through holes 112) assembly is inserted into each through hole 112, it should be appreciated that the nut is received by the first tier of through hole 112 and is prevented from entering the second tier of through hole 112 due to the reduced diameter of the second tier. Moreover, where the nut has a hexagonal shape similar to the first tier of the through hole, the nut is prevented from turning when the bolt is turned through the threading of the nut. Thus, when an elevator comprising the bolt and nut assembly is adjusted (e.g., bolt turned), the elevator is secured in place by the hexagonal first tier and raises or lowers that adjacent portion of mount 100 from a surface of the patient, for example head or skull.

Figure 4:
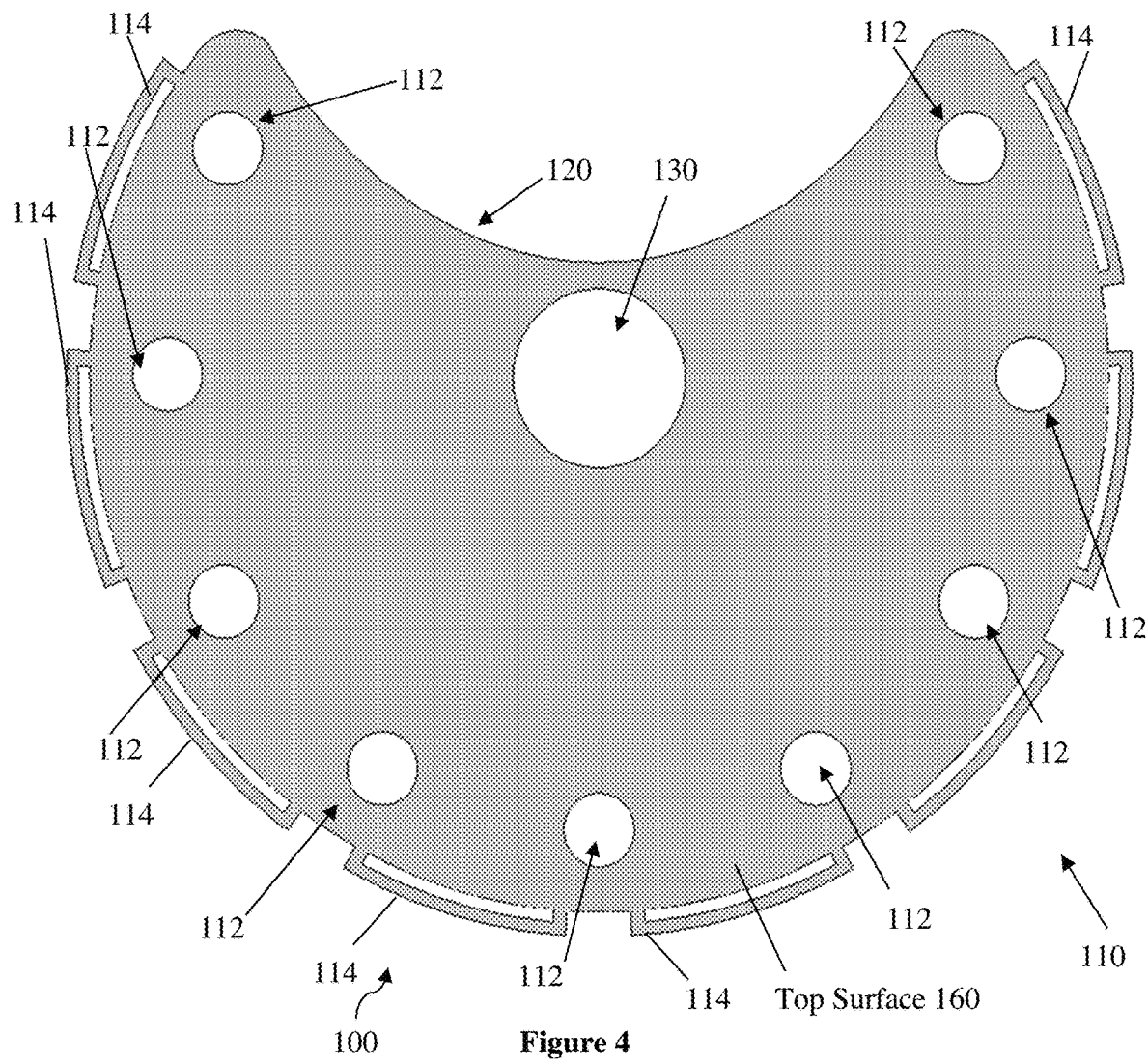
FIG. 4 depicts yet another view of the mount of FIG. 1.
Figure 5:
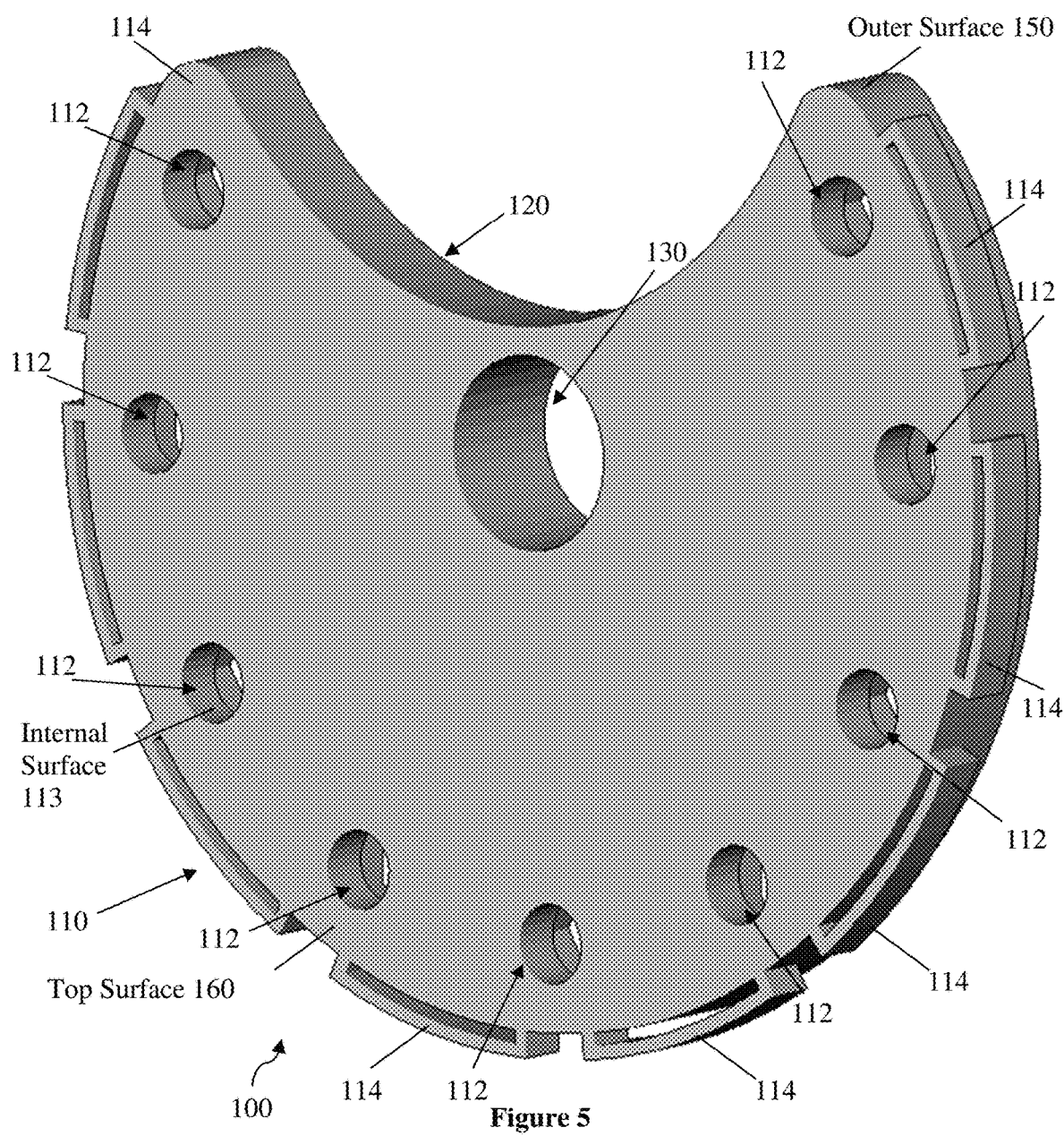
FIG. 5 depicts still another view of the mount of FIG. 1.
Figure 6:
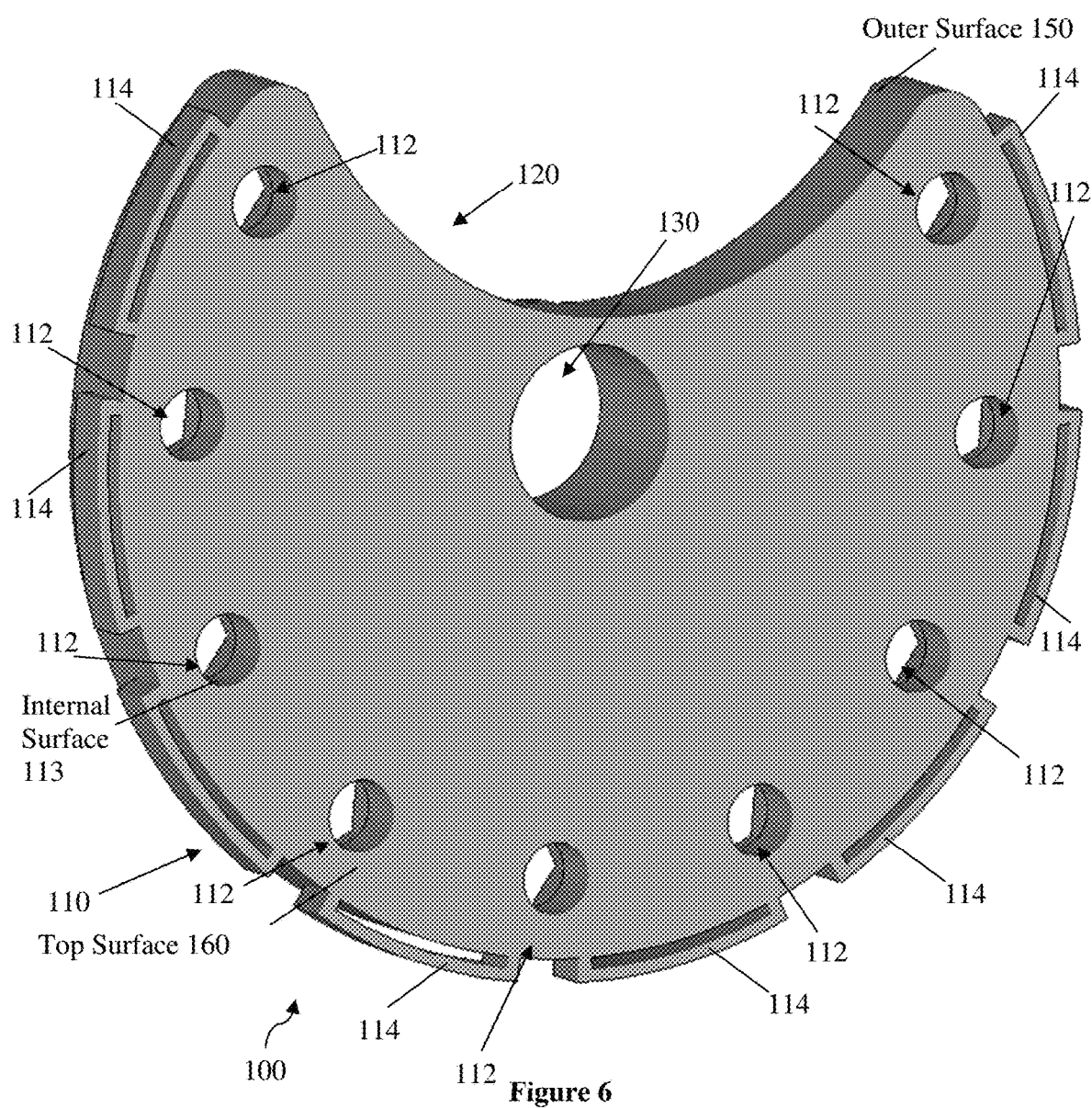
FIG. 6 depicts a further view of the mount of FIG. 1.

FIGS. 2-6 depict mount 100 of FIG. 1 from different perspectives, including body 110, through holes 112, supports 114, curved region 120, and channel 130 as previously described, with FIGS. 1-3 primarily showing perspectives of the bottom surface of mount 100, and FIGS. 4-6 primarily showing perspectives of the top surface of mount 100.

Figure 7:
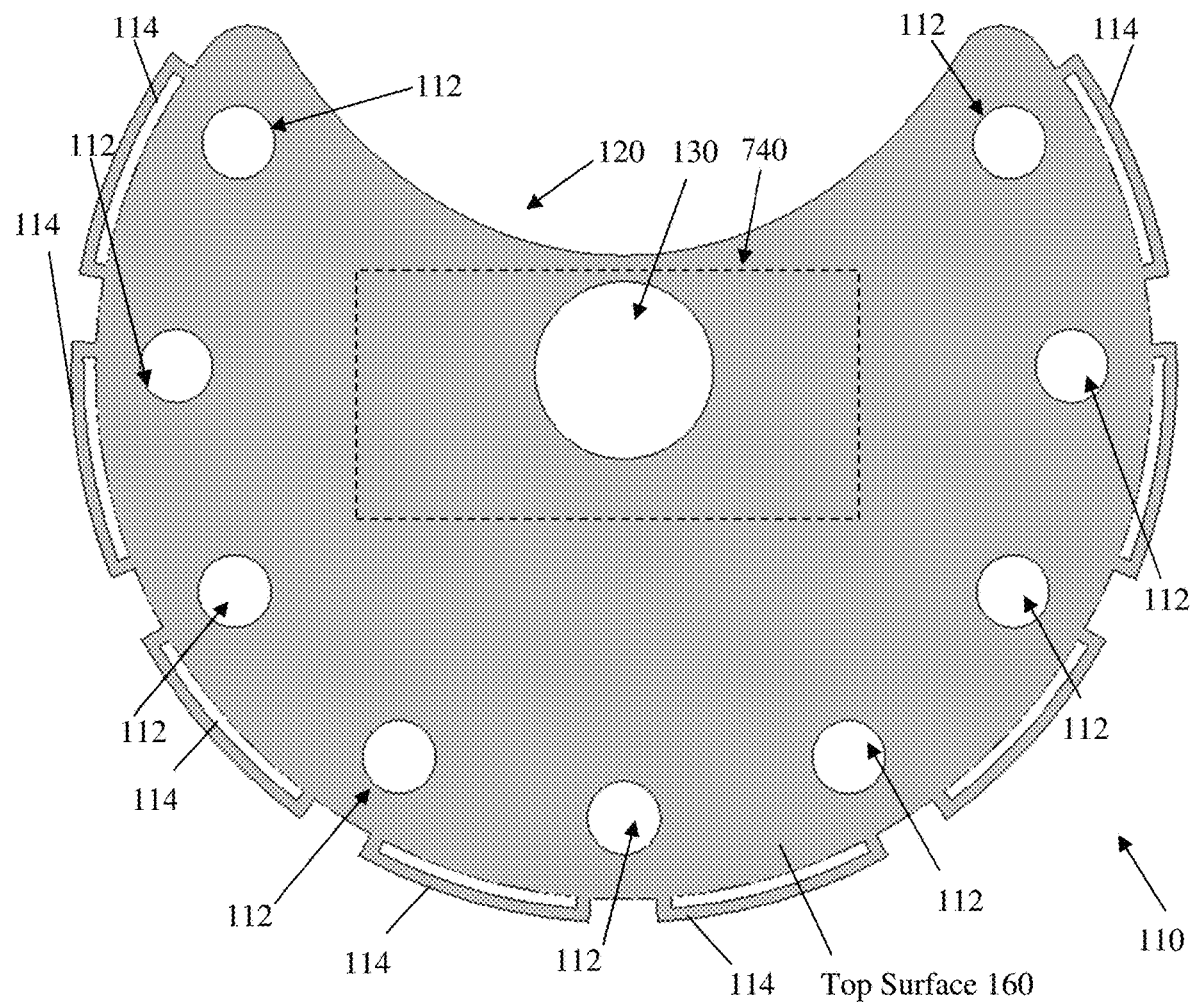
FIG. 7 depicts another mount of the inventive subject matter.

FIG. 7 depicts an alternative embodiment of the device depicted in FIGS. 1-6. Specifically, FIG. 7 depicts mount 700 in which two central channels 732 and 734 depicted in region 742 pass through mount 700 in region 740. Each channel 732 and 734 is designed to receive a transducer or at least a portion thereof (either two separate transducers, or two portions of a single transducer), with an operable portion of the transducer directed normal to the bottom surface of mount 700, for example toward a patient. In some embodiments, a single transducer includes two separate transducer heads or operable portions that extend through the two channels 732 and 734, while in other embodiments two separate transducers, each with its own operable portion, are used with mount 700. While FIG. 7 depicts the top surface of mount 700, it should be appreciated that the bottom surface of mount 700 includes a collar or raised lip around the perimeter of each of channels 732 and 734, similar to the collar or lip depicted in FIGS. 1-3. While the embodiment of FIG. 7 depicts two channels, it should be appreciated that devices of the inventive subject matter can accommodate three, four, or five transducers or operable transducer heads, for example via one, two, three, four, or five channels for receiving separate transducers, or with channels receiving or coupling with more than one transducer or operable transducer head.

The description includes information that may be useful in understanding the present invention. It is not an admission that any of the information provided herein is prior art, necessary, or relevant to the presently claimed invention, or that any publication specifically or implicitly referenced is prior art.

As used in the description herein and throughout the claims that follow, the meaning of "a," "an," and "the" includes plural reference unless the context clearly dictates otherwise. Also, as used in the description herein, the meaning of "in" includes "in" and "on" unless the context clearly dictates otherwise.

As used herein, and unless the context dictates otherwise, the term "coupled to" is intended to include both direct coupling (in which two elements that are coupled to each other contact each other) and indirect coupling (in which at least one additional element is located between the two elements). Therefore, the terms "coupled to" and "coupled with" are used synonymously.

Unless the context dictates the contrary, all ranges set forth herein should be interpreted as being inclusive of their endpoints, and open-ended ranges should be interpreted to include commercially practical values. Similarly, all lists of values should be considered as inclusive of intermediate values unless the context indicates the contrary.

The recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g. "such as") provided with respect to certain embodiments herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member can be referred to and claimed individually or in any combination with other members of the group or other elements found herein. One or more members of a group can be included in, or deleted from, a group for reasons of convenience and/or patentability. When any such inclusion or deletion occurs, the specification is herein deemed to contain the group as modified thus fulfilling the written description of all Markush groups used in the appended claims.

The following discussion provides many example embodiments of the inventive subject matter. Although each embodiment represents a single combination of inventive elements, the inventive subject matter is considered to include all possible combinations of the disclosed elements. Thus if one embodiment comprises elements A, B, and C, and a second embodiment comprises elements B and D, then the inventive subject matter is also considered to include other remaining combinations of A, B, C, or D, even if not explicitly disclosed.

It should be apparent to those skilled in the art that many more modifications besides those already described are possible without departing from the inventive concepts herein. The inventive subject matter, therefore, is not to be restricted except in the scope of the appended claims. Moreover, in interpreting both the specification and the claims, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced. Where the specification claims refers to at least one of something selected from the group consisting of A, B, C . . . and N, the text should be interpreted as requiring only one element from the group, not A plus N, or B plus N, etc.

What is claimed is:

1. A mount for affixing a device to a patient, comprising:
   a partial disk-shaped base having a top surface, a bottom surface, and an outer surface, wherein the partial disk-shaped base has a perimeter that is circular having a cutout;
   a plurality of through holes that pass through the top surface and the bottom surface of the partial disk-shaped base;
   a plurality of supports arranged along the outer surface of the partial disk-shaped base configured to affix the mount to the patient, and wherein each of the plurality of supports is separate from each of the plurality of through holes; and
   a channel that passes through the top surface and bottom surfaces of the partial disk-shaped base, wherein the channel is configured to receive the device.

2. The mount of claim 1, wherein the plurality of through holes are disposed about the perimeter of the partial disk-shaped base that is circular and thereby collectively form a U-shaped partially around the channel, and further wherein each of the plurality of through holes is configured to receive an elevator.

3. The mount of claim 2, wherein the plurality of through holes are evenly spaced, such that adjacent through holes within the plurality of the through holes are equidistant.

4. The mount of claim 1, wherein each of the plurality of through holes is configured to receive an elevator, and wherein an axis of each of the plurality of through holes is parallel with an axis of the channel.

5. The mount of claim 4, wherein each of the plurality of through holes comprises an elevator seat and a bore.

6. The mount of claim 5, wherein the elevator seat is positioned toward the bottom surface and the bore is positioned toward the top surface for each of the plurality of through holes.

7. The mount of claim 4, wherein an elevator seat of each of the plurality of through holes has a wider diameter than a bore of each of the plurality of through holes.

8. The mount of claim 1, wherein at least one of the plurality of supports is configured to couple with a strap.

9. The mount of claim 1, wherein the plurality of supports are positioned toward the top surface of the partial disk-shaped base along the outer surface.

10. The mount of claim 1, wherein the mount is configured to affix the device to the patient's head.

11. The mount of claim 1, wherein the device is an ultrasonic transducer.

12. The mount of claim 1, wherein a first support of the plurality of supports at least partially affixes the mount to the patient, and a second support of the plurality of supports at least partially affixes the device to the mount.

13. The mount of claim 1, wherein the channel directs an operable portion of the device normal to the bottom surface of the mount.

14. The mount of claim 1, wherein a bottom rim of the channel extends past the bottom surface.

15. The mount of claim 1, wherein at least some of the plurality of supports are disposed about the perimeter of the partial disk-shaped base that is circular.

16. The mount of claim 1, wherein the plurality of through holes are closer in distance to the channel than the plurality of supports.

17. The mount of claim 1, wherein the cutout of the perimeter of the partial disk-shaped base is curved.

18. The mount of claim 1, wherein each of the plurality of supports comprise a slot.

19. The mount of claim 1, wherein the channel is larger in size than each of the plurality of through holes.

\* \* \* \* \*